United States Patent [19]

Heckles

[11] 4,233,239

[45] Nov. 11, 1980

[54] UREADIACETOACETAMIDO COMPOUNDS

[75] Inventor: John S. Heckles, Lancaster, Pa.

[73] Assignee: Armstrong Cork Company, Lancaster, Pa.

[21] Appl. No.: 65,857

[22] Filed: Aug. 13, 1979

Related U.S. Application Data

[62] Division of Ser. No. 942,189, Sep. 14, 1978.

[51] Int. Cl.³ .......................................... C07C 127/00
[52] U.S. Cl. .................................... 564/57; 528/228; 564/58
[58] Field of Search ................................... 260/553 R

[56] References Cited

U.S. PATENT DOCUMENTS

| | | | |
|---|---|---|---|
| 3,017,388 | 1/1962 | Caldwell et al. | 528/228 |
| 3,053,804 | 9/1962 | Caldwell et al. | 528/228 X |
| 3,174,991 | 3/1965 | Steinbrunn | 260/553 R X |
| 3,192,261 | 6/1965 | Losee et al. | 260/553 R X |

FOREIGN PATENT DOCUMENTS

| | | | |
|---|---|---|---|
| 1240844 | 5/1967 | Fed. Rep. of Germany | 260/553 R |
| 1276025 | 8/1968 | Fed. Rep. of Germany | 260/553 R |

*Primary Examiner*—John Doll
*Attorney, Agent, or Firm*—Dennis M. Kozak

[57] ABSTRACT

Crosslinked random acrylate-ureadiacetoacetamide-diacetoacetamide copolymers are disclosed. These copolymers are prepared by the reaction of at least one polyfunctional acrylate with at least one ureadiacetoacetamide and at least one diacetoacetamide in the presence of a catalyst capable of promoting the reaction between the polyfunctional acrylate, the ureadiacetoacetamide, and the diacetoacetamide. In a preferred embodiment, the copolymers are employed to produce wear layer compositions for surface coverings.

6 Claims, No Drawings

UREADIACETOACETAMIDO COMPOUNDS

CROSS-REFERENCE TO RELATED APPLICATION

This is a division of application Ser. No. 942,189, filed Sept. 14, 1978.

This invention relates to polymers.

More specifically, this invention relates to acrylate-ureadiacetoacetamide-diacetoacetamide copolymers and to coatings or films produced from these copolymers.

In one of its more specific aspects, this invention pertains to crosslinked random copolymers which are the reaction products of polyfunctional acrylates, ureadiacetoacetamides, and diacetoacetamides.

The resilient flooring industry is continually searching for new abrasion-resistant polymeric compositions which will serve as wear layers for decorative surface coverings, especially thermoplastic floor coverings.

The present invention provides novel acrylate-ureadiaceto-acetamide-diacetoacetamide polymers which exhibit excellent film-forming properties and abrasion-resistant properties. Accordingly, these polymers, in film form, are well suited for use as wear layers for decorative thermoplastic floor coverings.

According to this invention, there is provided a crosslinked random acrylate-ureadiacetoacetamide-diacetoacetamide copolymer produced by the reaction of at least one polyfunctional acrylate with at least one ureadiacetoacetamide and at least one diacetoacetamide in the presence of a catalyst capable of promoting the reaction between the polyfunctional acrylate, the ureadiacetoacetamide, and the diacetoacetamide.

Also, according to this invention, there is provided a thermoplastic floor covering coated with a wear layer composition comprising a crosslinked random acrylate-ureadiacetoacetamide-diacetoacetamide copolymer produced by the reaction of at least one polyfunctional acrylate with at least one ureadiacetoacetamide and at least one diacetoacetamide in the presence of a catalyst capable of promoting the reaction between the polyfunctional acrylate, the ureadiacetoacetamide, and the diacetoacetamide.

It is to be understood that this invention also provides for the production of crosslinked acrylate-ureadiacetoacetamide copolymers, that is, copolymers prepared by the reaction of at least one polyfunctional acrylate with at least one ureadiacetoacetamide in the presence of a catalyst capable of promoting the reaction between the polyfunctional acrylate and the ureadiacetoacetamide. These acrylate-ureadiacetoacetamide copolymers have been found to exhibit film-forming properties which make the copolymers suitable for use to produce films or coatings. However, the resulting films or coatings tend to be rather hard, inflexible, and accordingly, not as well suited for use as wear layer compositions for thermoplastic floor coverings as are the acrylate-ureadiacetoacetamide-diacetoacetamide copolymers which facilitate the formation of more flexible wear layer coatings.

As the polyfunctional acrylate, use can be made of compounds having the formula $$R\text{-}(O\text{-}C(O)\text{-}CH=CH_2)_4,$$
$$R^1\text{-}(O\text{-}C(O)\text{-}CH=CH_2)_3, \text{ or}$$
$$R^2\text{-}(O\text{-}C(O)\text{-}CH=CH_2)_2$$

wherein R represents

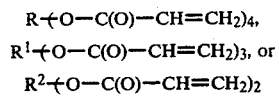

$R^1$ represents

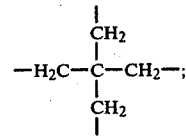

$R^2$ represents: a ($C_1$ to $C_{10}$) alkylene group, a ($C_1$ to $C_4$) alkyl substituted ($C_1$ to $C_{10}$) alkylene group,

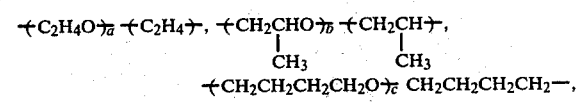

a cycloalkylene group, a cycloalkane bearing two ($C_1$ to $C_3$) alkylene groups,

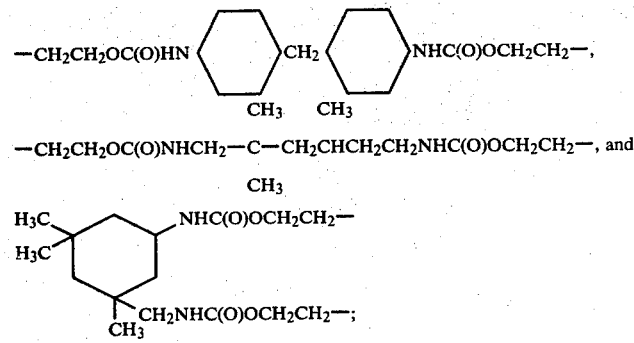

$R^3$ represents hydrogen or ($C_1$ to $C_3$) alkyl; a is an integer from 1 to 20; b is an integer from 1 to 10; and c is an integer from 1 to 5.

Representative of the above useable polyfunctional acrylates are trimethylol propane triacrylate, pentaerythritol tetraacrylate, hexane diol diacrylate, polyethylene glycol (200) diacrylate, ethylene glycol diacrylate, tripropylene glycol diacrylate, trimethyl hexane diol diacrylate, 1,4-cyclohexane dimethanol diacrylate, dibutylene glycol diacrylate, 1,4-cyclohexane diacrylate, dipropylene glycol di-2-acrylylethyl ether, methylenebis(4-cyclohexane-2-acrylyl-ethyl urethane) 2,2,4-trimethylhexanebis(2-acrylyl-ethyl urethane), isophorone di(2-acrylylethyl urethane), and the like.

The three above-recited urethane-containing diacrylates are not known to be commercially available. Accordingly, Examples 17 through 19 demonstrate a method for the preparation of each urethane-containing diacrylate recited above.

As the ureadiacetoacetamide, use can be made of compounds having the formula

H₃C—C(O)—CH₂—C(O)—NH—R⁴—NH—C-
(O)—HN—R⁵—NH—C(O)—HN—R⁴—NH—C-
(O)—CH₂—C(O)—CH₃ wherein $R^5$ represents: 2,2,4-trimethylhexamethylene, 2,4,4-trimethylhexamethylene, mixtures of 2,2,4-trimethylhexamethylene and 2,4,4-trimethylhexamethylene, methylenebis(4-cyclohexylene), and 3-methylene-3,5,5-trimethylcyclohexylene; wherein each $R^4$ may be the same or different and separately represents: a ($C_1$ to $C_{10}$) alkylene group, a ($C_1$ to $C_4$) alkyl substituted ($C_1$ to $C_{10}$) alkylene group,

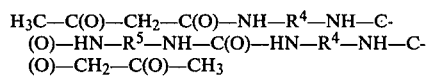

a cycloalkylene group, a cycloalkane bearing two ($C_1$ to $C_3$) alkylene groups,

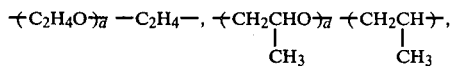

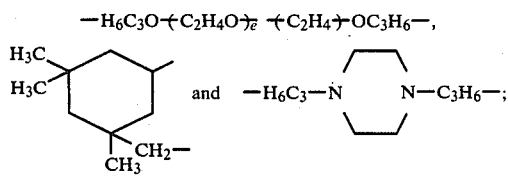

d is an integer from 1 to 6; and e is an integer from 1 to 4.

Representative of the above usable ureadiacetoacetamides are bis 1,3(1-acetoacetamide-2,2,4-trimethylhexamethylene-6-ureylene)3-methylene-3,5,5-trimethylcyclohexylene (hereinafter UDA-1); bis 4,4(1-acetoacetamide-2,2,4-trimethylhexamethylene-6-ureylene)1,1-methylenedicyclohexylene (hereinafter UDA-2); bis 1',6'(1-acetoacetamide-2,2,4-trimethylhexamethylene-6-ureylene)2,2,4-trimethylhexamethylene (hereinafter UDA-3); bis 1,6(1-acetoacetamide-1,4-dimethylenecyclohexane-4-ureylene)2,2,4-trimethylhexamethylene (hereinafter UDA-4); bis 4,4-(1-acetoacetamide-1,4-dimethylenecyclohexane-4-ureylene)1,1-methylenedicyclohexylene (hereinafter UDA-5); and bis 1,6-(1-acetoacetamide-1,3-dimethylenecyclohexane-4-ureylene)2,2,4-trimethylhexanemethylene (hereinafter UDA-6).

Unlike most of the polyfunctional acrylates, the ureadiacetoacetamides are not known to be commercially available. Accordingly, suitable methods for preparing the ureadiacetoacetamides usable in this invention are set forth in Examples 1 through 10 below.

As the diacetoacetamide, use can be made of compounds having the formula

R⁴—(NH—C(O)—CH₂—C(O)—CH₃)₂ wherein $R^4$, d, and e are as defined above.

Representative of the above usable diacetoacetamides are isophorone diacetoacetamide, diethylene glycol di-3-acetoacetamide propyl ether, N,N'-bis(propyl-3-acetoacetamide)-piperazine, 1,4 cyclohexanebis(methylacetoacetamide), 1,3 cyclohexanebis(methylacetoacetamide), 2,2,4-trimethylhexamethylenediacetoacetamide, 1,3-propanediacetoacetamide, diethyleneglycol-di-2-acetoacetamide-ethyl ether, dipropyleneglycol diacetoacetamide propyl ether, 1,4-cyclohexanebis(acetoacetamide), trimethylhexamethylene diacetoacetamide, and the like.

The above usable diacetoacetamides are not known to be commercially available. Accordingly, suitable methods for preparing the diacetoacetamides usable in this invention are set forth in Examples 11 through 16 below.

The amounts of polyfunctional acrylate, ureadiacetoacetamide, and diacetoacetamide can be varied within relatively wide ranges. Preferably, about 1 to about 2 moles of polyfunctional acrylate are employed for every mole of total ureadiacetoacetamide and diacetoacetamide. Best results are usually obtained in a mole ratio of from about 1.2 to about 1.4 moles of polyfunctional acrylate to about 1 mole of total ureadiacetoacetamide and diacetoacetamide. Preferably, the 1 mole of total ureadiacetoacetamide and diacetoacetamide will comprise ureadiacetoacetamide in an amount of from about 0.1 mole to about 0.9 mole and diacetoacetamide in an amount of from about 0.1 mole to about 0.9 mole.

Although the ureadiacetoacetamides and the diacetoacetamides can be separately prepared, it is preferred, as demonstrated in Examples 1–10, that both ureadiacetoacetamide and diacetoacetamide be prepared in a single reaction rather than being prepared by separate reactions.

As the catalyst to promote the reaction, a Michael reaction, use can be made of any of a variety of well known Michael reaction-type catalysts commonly employed to promote condensation. Particularly suitable are strong basic catalysts such as sodium methoxide, sodium metal, sodium ethylate, benzyl-trimethyl ammonium methoxide, and the like. Catalytic amounts of materials are selected in accordance with well known practices in the polymer art, the amount being one sufficient to promote the polycondensation reaction. For further information relating to the Michael reaction mechanism, see "The Michael Reaction" by E. D. Bergmann et al., *Organic Reactions*, Vol. 10, chapter 3, pages 179–555, and *Modern Synthetic Reactions*, H. O. House, 2nd Ed. (1972), pages 595–623, both herein incorporated by reference.

The polymerization reaction can be carried out using the reactants as the only reaction medium since both the polyfunctional acrylates, the ureadiacetoacetamides, and the diacetoacetamides are normally in the liquid state and/or they can be uniformly blended together.

Further, if the acrylate-ureadiacetoacetamide-diacetoacetamide copolymer is employed to produce a wear layer composition, the polymerization reaction can be carried out in the presence of art recognized amounts of optional ingredients typically employed in wear layer compositions such as surfactants, heat and light stabilizers, and the like.

The following examples will serve to more fully illustrate specific embodiments of and the best mode for practicing this invention.

EXAMPLE 1

This example demonstrates the preparation of a mixture containing ureadiacetoacetamide and diacetoacetamide.

To a reaction vessel were added about 17 grams (0.065 mole) of methylene bis-4-cyclohexyl isocyanate (designated "Hylene W" commercially available from E. I. DuPont) in about 30 milliliters of methylene chloride and about 58 grams (0.39 mole) of 2,2,4-trimethylhexanediamine in about 260 milliliters of methylene chloride with stirring.

The contents of the reaction vessel were cooled to and maintained at a temperature of from 10° to 15° C. and about 55 grams (0.65 mole) of diketene were added to the contents of the reaction vessel with cooling to 5° to 10° C.

The contents of the reaction vessel were held at a temperature of from 5° to 15° C. for about 4½ hours and then about 6 grams of isopropylamine were added to the contents of the reaction vessel.

The resulting reaction product was transferred to a separatory funnel and acidified with dilute hydrochloric acid.

The reaction product was washed twice, once with about 250 milliliters of water and about 50 milliliters of saturated sodium chloride solution and a second time with about 250 milliliters of water, about 50 milliliters of saturated sodium chloride solution and a sufficient amount (about 5 cc) of saturated $NaHCO_3$ solution to neutralize the separatory funnel contents to a pH of about 6.

After the second washing, the methylene chloride layer containing the reaction product was dried with anhydrous magnesium sulfate. The magnesium sulfate was filtered off; the methylene chloride removed by vacuum distillation, and the resulting product observed, analyzed, and found to be a light yellow viscous mixture of 0.2 mole of UDA-2 and 0.8 mole of trimethylhexanediacetoacetamide. The yield was 119.4 grams.

EXAMPLE 2

This example demonstrates the preparation of a mixture containing ureadiacetoacetamide and diacetoacetamide.

To a reaction vessel were added about 9.7 grams (0.044 mole) isophorone diisocyanate (3-isocyanatomethyl-3,5,5-trimethylcyclohexylisocyanate) in about 25 milliliters of methylene chloride and about 44.3 grams (0.3 mole) trimethylhexanediamine in about 230 milliliters of methylene chloride with stirring.

The contents of the reaction vessel were cooled to and maintained at a temperature of from 10° to 15° C. and about 41.3 grams (0.49 mole) of diketene were added to the contents of the reaction vessel with cooling to about 10° C.

The contents of the reaction vessel were held at about 10° C. for about 3 hours.

The resulting reaction product was transferred to a separatory funnel and acidified with dilute hydrochloric acid.

The reaction product was washed twice, once with about 250 milliliters of water and about 50 milliliters of saturated sodium chloride solution and a second time with about 250 milliliters of water, about 50 milliliters of saturated sodium chloride solution and a sufficient amount (about 5 cc) of saturated $NaHCO_3$ solution to neutralize the separatory funnel contents to a pH of about 6.

After the second washing, the methylene chloride layer containing the reaction product was dried with anhydrous magnesium sulfate. The magnesium sulfate was filtered off; the methylene chloride removed by vacuum distillation, and the resulting product observed, analyzed, and found to be a light yellow viscous mixture of 0.2 mole of UDA-1 and 0.8 mole of trimethylhexanediacetoacetamide. The yield was 84.5 grams.

EXAMPLE 3

This example demonstrates the preparation of a mixture containing ureadiacetoacetamide and diacetoacetamide using the following ingredients and substantially the procedure of Example 1.

Ingredients 26 grams (0.12 mole) trimethylhexane diisocyanate (TMDI) in 70 milliliters $CH_2Cl_2$
63 grams (0.43 mole) trimethylhexanediamine (TMDA) in 300 milliliters $CH_2Cl_2$
55.5 grams (0.66 mole) diketene The resulting reaction product was viscous, yellow in color, analyzed and found to contain 0.3 mole of UDA-3 and 0.7 mole of trimethylhexanediacetoacetamide. The yield was 134.2 grams.

EXAMPLE 4

This example demonstrates the preparation of a mixture containing ureadiacetoacetamide and diacetoacetamide using the following ingredients and substantially the procedure of Example 1.

Ingredients 26 grams (0.12 mole) trimethylhexanediisocyanate (TMDI) in 50 milliliters $CH_2Cl_2$
44.4 grams (0.31 mole) trimethylhexanediamine (TMDA) in 210 milliliters $CH_2Cl_2$
33.6 grams (0.40 mole) diketene The resulting reaction product was viscous, yellow in color, analyzed, and found to contain 0.5 mole of UDA-3 and 0.5 mole of trimethylhexanediacetoacetamide. The yield was 96 grams.

EXAMPLE 5

This example demonstrates the preparation of a mixture containing ureadiacetoacetamide and diacetoacetamide using the following ingredients and substantially the procedure of Example 1.

Ingredients 31.2 grams (0.15 mole) trimethylhexanediisocyanate (TMDI) in 50 milliliters $CH_2Cl_2$
41.5 grams (0.28 mole) trimethylhexanediamine (TMDA) in 200 milliliters $CH_2Cl_2$
28.2 grams (0.34 mole) diketene The resulting reaction product was viscous, yellow in color, analyzed and found to contain 0.75 mole of UDA-3 and 0.25 mole of trimethylhexanediacetoacetamide. The yield was 105 grams.

EXAMPLE 6

This example demonstrates the preparation of a mixture containing ureadiacetoacetamide and diacetoacetamide using the following ingredients and substantially the procedure of Example 1.

Ingredients 8.7 grams (0.034 mole) "Hylene W" (methylene bis-4-cyclohexyl isocyanate) in 20 milliliters $CH_2Cl_2$
30.8 grams (0.21 mole) trimethylhexanediamine (TMDA) in 135 milliliters $CH_2Cl_2$
27.3 grams (0.33 mole) diketene The resulting reaction product was viscous, yellow in color, analyzed and found to contain 0.2 mole of UDA-2 and 0.8 mole of trimethylhexanediacetoacetamide. The yield was 69.6 grams.

EXAMPLE 7

This example demonstrates the preparation of a mixture containing ureadiacetoacetamide and diacetoacetamide using the following ingredients and substantially the procedure of Example 1.

Ingredients 18.2 grams (0.086 mole) trimethylhexanediisocyanate (TMDI) in 20 milliliters $CH_2Cl_2$
10.7 grams (0.07 mole) trimethylhexanediamine and
19.9 grams (0.14 mole) 1,3-cyclohexylbismethylamine in 200 milliliters $CH_2Cl_2$
13.8 grams (0.09 mole) trimethylhexanediamine
39.4 grams (0.47 mole) diketene The resulting reaction product was viscous, yellow in color, analyzed and found to contain 0.3 mole mixed UDA-3 and UDA-6 and 0.7 mole of trimethylhexanediacetoacetamide. The yield was 95 grams.

EXAMPLE 8

This example demonstrates the preparation of a mixture containing ureadiacetoacetamide and diacetoacetamide using the following ingredients and substantially the procedure of Example 1.

Ingredients 26 grams (0.12 mole) trimethylhexanediisocyanate (TMDI) in 50 milliliters $CH_2Cl_2$
19.8 grams (0.13 mole) trimethylhexanediamine and
14.3 grams (0.10 mole) 1,4-cyclohexylbismethylamine in 200 milliliters $CH_2Cl_2$
24.8 grams (0.27 mole) diketene The resulting reaction product was viscous, yellow in color, analyzed and found to contain 0.75 mole of mixed UDA-3 and UDA-4 and 0.25 mole of trimethylhexanediacetoacetamide. The yield was 83 grams.

EXAMPLE 9

This example demonstrates the preparation of a mixture containing ureadiacetoacetamide and diacetoacetamide using the following ingredients and substantially the procedure of Example 1.

Ingredients 26 grams (0.10 mole) "Hylene W" (methylene bis-4-cyclohexylisocyanate) in 40 milliliters $CH_2Cl_2$
18.5 grams (0.13 mole) trimethylhexanediamine and
14.2 grams (0.10 mole) 1,4-cyclohexylbismethylamine in 500 milliliters $CH_2Cl_2$
80.2 grams (0.54 mole) trimethylhexanediamine
114.4 grams (1.36 mole) diketene The resulting reaction product was viscous, yellow in color, analyzed and found to contain 0.15 mole of mixed UDA-2 and UDA-5 and 0.85 mole of trimethylhexanediacetoacetamide. The yield was 250 grams.

EXAMPLE 10

This example demonstrates the preparation of a mixture containing ureadiacetoacetamide and diacetoacetamide using the following ingredients and substantially the procedure of Example 1.

Ingredients 31 grams (0.12 mole) "Hylene W" (methylene bis-4-cyclohexylisocyanate) in 50 milliliters $CH_2Cl_2$
136 grams (0.92 mole) 2,2,4-trimethylhexamethylenediamine in 250 milliliters $CH_2Cl_2$
137 grams (1.63 moles) diketene The resulting reaction product was viscous, yellow in color, analyzed and found to contain 0.15 mole of UDA-2 and 0.85 mole of trimethylhexamethylenediacetoacetamide. The yield was 276 grams.

EXAMPLE 11

This example demonstrates a method for the preparation of isophorone diacetoacetamide.

About 85 grams (0.5 mole) of isophorone diamine (3-aminomethyl 3,5,5-trimethylcyclohexylamine) and about 325 milliliters of methylene chloride were added to a reaction vessel with stirring.

The contents of the reaction vessel were cooled to and maintained at a temperature of about 15° C. and about 80 grams (0.95 mole) of diketene were added to the contents of the reaction vessel over a period of about 1 hour.

The temperature of the contents of the reaction vessel was held at about 15° C. for about 1¾ hours and the resulting reaction product was transferred to a separatory funnel and acidified with dilute hydrochloric acid.

The reaction product was washed twice, once with about 250 milliliters of water and about 50 milliliters of saturated sodium chloride solution and a second time with about 250 milliliters of water, about 50 milliliters of saturated sodium chloride solution and a sufficient amount (about 5 cc) of saturated $NaHCO_3$ solution to neutralize the separatory funnel contents to a pH of about 6.

After the second washing, the methylene chloride layer containing the reaction product was dried with anhydrous magnesium sulfate. The magnesium sulfate was filtered off; the methylene chloride was removed by vacuum distillation and the resulting product, isophorone diacetoacetamide, was recovered in a yield of about 132 grams and observed to be viscous and light yellow in color.

EXAMPLE 12

This example demonstrates a method for the preparation of diethyleneglycol diacetoacetamide propyl ether.

About 66 grams (0.3 mole) of diethyleneglycol diaminopropyl ether (commercially available from Union Carbide Corporation, designated "Polyglycoldiamine H-221") and about 230 milliliters of methylene chloride were added to a reaction vessel with stirring.

The contents of the reaction vessel were cooled to and maintained at a temperature of about 15° C. and about 50.4 grams (0.6 mole) of diketene were added to the contents of the reaction vessel over a period of about 1 hour.

The temperature of the contents of the reaction vessel was held at about 10° to 15° C. for a period of about 4 hours and the methylene chloride was removed by vacuum distillation.

The resulting reaction product was dissolved in isopropyl alcohol and recrystallized from the alcohol. The resulting product, diethyleneglycol diacetoacetamide propyl ether, was recovered and found to have a melting point range of about 62° to 63° C. and observed to be white in color.

EXAMPLE 13

This example demonstrates a method for the preparation of N,N'-bis(propyl-3-acetoacetamide)-piperazine.

The following ingredients were reacted using substantially the procedure of Example 11 with the exception that the contents of the reaction vessel were held at 10° to 15° C. for a period of about 4 hours instead of the 1¾ hours in Example 11.

| Ingredients | Amount |
|---|---|
| diketene | 50.4 grams (0.6 mole) |
| N,N'-bis(aminopropyl)-piperazine | 60 grams (0.3 mole) |
| methylene chloride | 250 milliliters |

The resulting product, N,N'-bis(propyl-3-acetoacetamide)piperazine, was recovered in a yield of about 92 grams and observed to be viscous and light yellow in color.

EXAMPLE 14

This example demonstrates a method for the preparation of 1,4-cyclohexanebis(methylacetoacetamide).

The following ingredients were reacted using substantially the procedure of Example 12 with the exception that the contents of the reaction vessel were held at about 15° C. for about 2 hours.

| Ingredients | Amount |
|---|---|
| diketene | 33.6 grams (0.4 mole) |
| 1,4 cyclohexanebis(methylamine) | 28.4 grams (0.2 mole) |
| methylene chloride | 100 milliliters |

The resulting crude product, 1,4-cyclohexanebis(methylacetoacetamide), was recovered and recrystallized from isopropyl alcohol. The recrystallized product was found to have a melting point range of about 140° to 143° C. and observed to be white in color.

EXAMPLE 15 .

This example demonstrates a method for the preparation of 1,3-cyclohexanebis(methylacetoacetamide).

The following ingredients were reacted using substantially the procedure of Example 12 with the exception that chloroform was substituted for the methylene chloride, and rather than recrystallizing in isopropyl alcohol, the reaction product was washed in benzene.

| Ingredients | Amount |
|---|---|
| diketene | 84 grams (1 mole) |
| 1,3-cyclohexanebis(methylamine) | 71 grams (0.5 mole) |
| chloroform | 250 milliliters |

The benzene insoluble fraction of the reaction product was recovered as 1,3-cyclohexanebis(methylacetoacetamide) and found to have a melting point range of about 105° to 115° C. and observed to be light yellow in color.

EXAMPLE 16

This example demonstrates a method for the preparation of 2,2,4-trimethylhexamethylenediacetoacetamide.

The following ingredients were reacted using substantially the procedure of Example 11 with the exception that the contents of the reaction vessel were held at 10° to 15° C. for a period of about 2 hours instead of the 1¾ hours in Example 11.

| Ingredients | Amount |
|---|---|
| diketene | 49.2 grams (0.59 mole) |
| trimethylhexanediamine | 45.3 grams (0.31 mole) |
| methylene chloride | 150 milliliters |

The resulting product, 2,2,4-trimethylhexamethylenediacetoacetamide, was recovered in a yield of about 89 grams and observed to be light yellow in color and viscous.

EXAMPLE 17

This example demonstrates the preparation of a urethane-containing diacrylate.

About 1 mole of methylenebis-4-cyclohexane isocyanate (designated "Hylene W", commercially available from E. I. DuPont de Nemours Co.) and about 2 moles of hydroxyethylacrylate and about 0.05 gram of dibutyltin dilaurate catalyst were added to a reaction vessel at room temperature, with stirring. The temperature of the reaction vessel was increased to about 60° C. After about 3 hours, the resulting reaction product, methylenebis(4-cyclohexane-2-acryl-ethyl urethane), having the formula

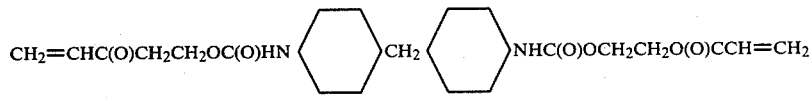

was recovered.

EXAMPLE 18

This example demonstrates the preparation of a urethane-containing diacrylate.

About 1 mole of 2,2,4-trimethylhexane diisocyanate (designated "TMDI", commercially available from Thorson Chemical Co.) and about 2 moles of hydroxyethylacrylate and about 0.05 gram of dibutyltin dilaurate catalyst were added to a reaction vessel at room temperature, with stirring. The temperature of the reaction vessel was increased to about 60° C. After about 3 hours, the resulting reaction product, 2,2,4-trimethylhexane-bis(2-acrylyl-ethyl urethane), having the formula

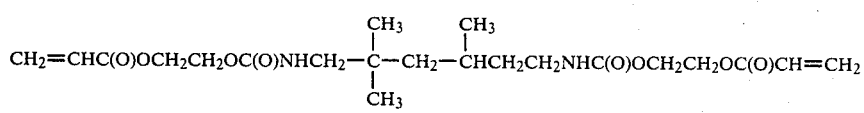

was recovered.

EXAMPLE 19

This example demonstrates the preparation of a urethane-containing diacrylate.

About 1 mole of 3-isocyanatomethyl-3,5,5-trimethylcyclohexyl isocyanate (designated "IPDI" isophorone diisocyanate, commercially available from Thorson Chemical Co.) and about 2 moles of hydroxyethylacrylate and about 0.05 gram of dibutyltin dilaurate catalyst were added to a reaction vessel at room temperature, with stirring. The temperature of the reaction vessel was increased to about 60° C. After about 3 hours, the resulting reaction product, isophorone di(2-acrylylethyl urethane), having the formula

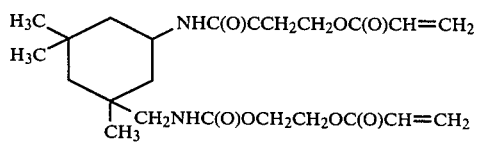

was recovered.

EXAMPLE 20

This example demonstrates the preparation of a polymer film of this invention.

About 1.2 moles of hexanediol diacrylate, about 1.0 mole diacetoacetamide of the reaction product mixture of Example 1 (contains 0.2 mole UDA-2), about 0.4 percent by weight of the reactants of a 30% by weight polyethyleneoxide siloxane surfactant (Dow Corning DC-193) in methanol solution and about 0.3 percent by weight of the reactants of a 15% by weight sodium methoxide in methanol catalyst solution were added to a reaction vessel at room temperature with stirring.

The resulting polymer mixture was coated on a glass surface using a Bird applicator to a coating thickness of about 0.003 inch.

The coating was non-tacky after about 1 hour and was allowed to cure for about 16 hours at a temperature of about 60° C.

The resulting cured polymer film was removed from the glass surface and observed to be clear and colorless. The film was tested by differential scanning calorimetery (DuPont 900 Thermal Analyzer) and found to have a Tg midpoint of about 36° C. The cured polymer film was also found to have a tensile strength of 3,330 psi and a percent elongation of 171.

EXAMPLE 21

The following ingredients were reacted using substantially the procedure of Example 20.

| Ingredients | Amount |
| --- | --- |
| hexanediol diacrylate | 1.4 moles |
| reaction product mixture of Example 1 | 1.0 mole |
| 30% by weight "DC-193" in methanol solution | 0.4% by weight |
| 15% by weight sodium methoxide in methanol catalyst solution | 0.3% by weight |

The resulting mixture was coated on a glass surface and cured at about 60° C. for about 16 hours.

The resulting cured polymer film was removed from the glass surface and observed to be clear and colorless. The film was tested and found to have a Tg midpoint of about 42° C. The polymer film was also found to have a tensile strength of 4,150 psi and a percent elongation of 108.

EXAMPLE 22

The following ingredients were reacted using substantially the procedure of Example 20.

| Ingredients | Amount |
| --- | --- |
| hexanediol diacrylate | 1.6 moles |
| reaction product mixture of Example 1 | 1.0 mole |
| 30% by weight "DC-193" in methanol solution | 0.4% by weight |
| 15% by weight sodium methoxide in methanol catalyst solution | 0.3% by weight |

The resulting mixture was coated on a glass surface and cured at about 60° C. for about 16 hours.

The resulting cured polymer film was removed from the glass surface and observed to be clear and colorless. The film was tested and found to have a Tg midpoint of about 44° C. The polymer film was also found to have a tensile strength of 2,890 psi and a percent elongation of 30.

The following Table I contains Examples 23 through 25. All polymer compositions were prepared using substantially the procedure of Example 20. All examples were catalyzed with 1 percent by weight of a 15 percent by weight sodium methoxide in methanol solution and included 0.4 percent by weight of a 30 percent by weight "DC-193" in methanol solution surfactant.

TABLE I

Cured Polymer Films of 1.0 Mole of the Reaction Product Mixture of Example 1 (U-1) With Hexanediol Diacrylate (HDDA) and Tripropyleneglycol Diacrylate (TPGDA)

| Example No. | Ingredients and Amount (Moles) | | | Tg (DSC) Midpoint | Tensile Strength PSI | Percent Elongation |
| --- | --- | --- | --- | --- | --- | --- |
| 23 | 1.0M U-1 | 1.2M HDDA | 2M TPGDA | 37° | 2,770 | 113 |
| 24 | 1.0M V-1 | 1.0M HDDA | .4M TPGDA | 32° | 2,420 | 163 |
| 25 | 1.0M U-1 | .8M HDDA | .6M TPGDA | 23° | 1,410 | 241 |

The following Table II contains Examples 26 and 27. Both polymer compositions were prepared using substantially the procedure of Example 20. Both examples were catalyzed with 1 percent by weight of a 15 percent by weight sodium methoxide in methanol solution and included 0.4 percent by weight of a 30 percent by weight "DC-193" in methanol solution surfactant.

TABLE II

Cured Polymer Films of 1.0 Mole of the Reaction Product Mixture of Example 3 (U-3) With Hexanediol Diacrylate (HDDA)

| Example No. | Ingredients and Amount (Moles) | | Tg (DSC) Midpoint | Tensile Strength PSI | Percent Elongation |
|---|---|---|---|---|---|
| 26 | 1.0M U-3 | 1.2M HDDA | 37° | 1,490 | 309 |
| 27 | 1.0M U-3 | 1.4M HDDA | 33° | 1,940 | 241 |

The following Table III contains Examples 28 through 32. All polymer compositions were prepared using substantially the procedure of Example 20. All examples were catalyzed with 1 percent by weight of a 15 percent by weight sodium methoxide in methanol solution and included 0.4 percent by weight of a 30 percent by weight "DC-193" in methanol solution surfactant.

TABLE III

Cured Polymer Films of 1.0 Mole of the Reaction Product Mixture of Example 4 (U-4) With Hexanediol Diacrylate (HDDA) and Tripropyleneglycol Diacrylate (TPGDA)

| Example No. | Ingredients and Amount (Moles) | | | Tg (DSC) Midpoint | Tensile Strength PSI | Percent Elongation |
|---|---|---|---|---|---|---|
| 28 | 1.0M U-4 | 1.2M HDDA | | 30° | 2,920 | 200 |
| 29 | 1.0M U-4 | 1.4M HDDA | | 21° | 2,670 | 132 |
| 30 | 1.0M U-4 | 1.6M HDDA | | 41° | 2,890 | 11 |
| 31 | 1.0M U-4 | 1.2M HDDA | .2M TPGDA | 32° | 3,850 | 167 |
| 32 | 1.0M U-4 | 1.0M HDDA | .4M TPGDA | 31° | 3,550 | 244 |

The following Table IV contains Examples 33 through 38. All polymer compositions were prepared using substantially the procedure of Example 20. All examples were catalyzed with 1 percent by weight of a 15 percent by weight sodium methoxide in methanol solution and included 0.4 percent by weight of a 30 percent by weight "DC-193" in methanol solution surfactant.

TABLE IV

Cured Polymer Films of 1.0 Mole of the Reaction Product Mixture of Example 5 (U-5) With Hexanediol Diacrylate (HDDA), Tripropyleneglycol Diacrylate (TPGDA), and Polyethyleneglycol Diacrylate (PEG200DA)

| Example No. | Ingredients and Amount (Moles) | | | Tg (DSC) Midpoint | Tensile Strength PSI | Percent Elongation |
|---|---|---|---|---|---|---|
| 33 | 1.0M U-5 | 1.4M HDDA | | 44° | 3,290 | 60 |
| 34 | 1.0M U-5 | 1.2M HDDA | .2M TPGDA | 37° | 3,740 | 131 |
| 35 | 1.0M U-5 | .8M HDDA | .4M TPGDA | 36° | 3,670 | 177 |
| 36 | 1.0M U-5 | 1.2M HDDA | .2M PEG200DA | 36° | 4,100 | 172 |
| 37 | 1.0M U-5 | 1.0M HDDA | .4M PEG200DA | 32° | 3,990 | 210 |
| 38 | 1.0M U-5 | .8M HDDA | .6M PEG200DA | 31° | 4,100 | 263 |

EXAMPLE 39

This example demonstrates the preparation of a polymer film of this invention using the reaction product mixture of Example 7. About 3.5 grams of the reaction product mixture of Example 7, about 2.6 grams hexanediol diacrylate, about 1 gram methanol, about 0.03 gram 30% DC-193 in methanol and about 0.06 gram 15% sodium methoxide in methanol were added to a reaction vessel at room temperature, with stirring.

A 0.003" film of the resulting polymer mixture was drawndown on a glass plate and cured 16 hours at 60° C.

The resulting cured film was stripped from the glass and was observed to be clear and glossy. The cured film was tested and found to have a tensile strength of 2,600 psi, a percent elongation of 72% and a Tg range of 28°–48° with a midpoint of 38°. The film was found to be fairly resistant to scratching by steel wool.

The following Table V contains Examples 40 through 42. All polymer compositions were prepared using substantially the procedure of Example 20. All examples were catalyzed with 1 percent by weight of a 15 percent by weight sodium methoxide in methanol solution and included 0.4 percent by weight of a 30 percent by weight "DC-193" in methanol solution surfactant.

TABLE V

Cured Polymer Films of 1.0 Mole of the Reaction Product Mixture of Example 8 (U-8) With Hexanediol Diacrylate (HDDA) and Polyethyleneglycol 200 Diacrylate (PEG200DA)

| Example No. | Ingredients and Amount (Moles) | | | Tg (DSC) Midpoint | Tensile Strength PSI | Percent Elongation |
|---|---|---|---|---|---|---|
| 40 | 1.0M U-8 | 1.2M HDDA | .2M PEG200DA | 39° | 4,200 | 31 |
| 41 | 1.0M U-8 | 1.0M HDDA | .4M PEG200DA | 35° | 4,360 | 179 |

TABLE V-continued

Cured Polymer Films of 1.0 Mole of the
Reaction Product Mixture of Example 8 (U-8) With
Hexanediol Diacrylate (HDDA) and
Polyethyleneglycol 200 Diacrylate (PEG200DA)

| Example No. | Ingredients and Amount (Moles) | | | Tg (DSC) Midpoint | Tensile Strength PSI | Percent Elongation |
|---|---|---|---|---|---|---|
| 42 | 1.0M U-8 | .8M HDDA | .6M PEG200DA | 34° | 3,990 | 149 |

EXAMPLE 43

This example demonstrates the preparation of a polymer film of this invention using the reaction product mixture of Example 2. About 5.3 grams of the reaction product mixture of Example 2, about 3.8 grams hexanediol diacrylate, about 0.5 gram isopropyl alcohol, about 0.04 gram 30% DC-193 in methanol and about 0.07 gram 40% benzyltrimethylammonium methoxide in methanol were added to a reaction vessel at room temperature, with stirring.

A 0.003" film of the resulting polymer mixture was drawndown on a glass plate and cured 16 hours at 60°.

The resulting cured film was stripped from the glass and was observed to be inflexible, glossy, and yellow in color. The cured film was tested and found to have a Tg range of 31°-51° with a Tg midpoint of 41° and was found to be fairly resistant to scratching by steel wool.

EXAMPLE 44

This example demonstrates the preparation of a thermoplastic floor covering which was coated with a wear layer composition comprising a cross-linked random acrylate-ureadiacetoacetamide-diacetoacetamide copolymer of this invention.

About 11.9 grams of hexanediol diacrylate, about 15.1 grams of the reaction product mixture of Example 1 and 0.19 gram of a 40% by weight benzyltrimethyl ammonium methoxide in methanol catalyst solution were added to a mixing vessel with stirring at room temperature.

The resulting wear layer composition was applied using a conventional applicator, in this example a Bird applicator, to a 12"×12" white vinyl tile and cured at 60° C. for about 16 hours.

The resulting cured acrylate-ureadiacetoacetamide-diacetoacetamide copolymer wear layer on the tile was observed to be clear and colorless.

The wear layer coated tile was tested for gloss retention using an art recognized traffic wheel test. The initial gloss value, before testing, was 90. After 30 minutes of testing, the gloss value was 73. After 60 minutes of testing, the gloss value was 71. And after 90 minutes of testing, the gloss value was 71. The wear layer was also subjected to an art recognized steel wool scratch test and found to exhibit good scratch resistance.

It will be evident from the foregoing that various modifications can be made to the present invention. Such, however, are considered as being within the scope of this invention.

What is claimed is:

1. bis 1,3(1-acetoacetamide-2,2,4-trimethylhexamethylene-6-ureylene)3-methylene-3,5,5-trimethylcyclohexylene.

2. bis 4,4(1-acetoacetamide-2,2,4-trimethylhexamethylene-6-ureylene)1,1-methylenedicyclohexylene.

3. bis 1',6'(1-acetoacetamide-2,2,4-trimethylhexamethylene-6-ureylene)2,2,4-trimethylhexamethylene.

4. bis 1,6(1-acetoacetamide-1,4-dimethylenecyclohexane-4-ureylene)2,2,4-trimethylhexamethylene.

5. bis 4,4-(1-acetoacetamide-1,4-dimethylenecyclohexane-4-ureylene)1,1-methylenedicyclohexylene.

6. bis 1,6-(1-acetoacetamide-1,3-dimethylenecyclohexane-4-ureylene)2,2,4-trimethylhexamethylene.

* * * * *